(12) United States Patent
Shafer et al.

(10) Patent No.: US 7,230,005 B2
(45) Date of Patent: Jun. 12, 2007

(54) COMPOUNDS AND METHODS FOR LOWERING THE ABUSE POTENTIAL AND EXTENDING THE DURATION OF ACTION OF A DRUG

(75) Inventors: Jules A. Shafer, Gwynedd Valley, PA (US); Vladislav V. Telyatnikov, Hatfield, PA (US); Zhiwei Guo, Franklin Park, NJ (US)

(73) Assignee: Controlled Chemicals, Inc., Colmar, PA (US)

( * ) Notice: Subject to any disclaimer, the term of this patent is extended or adjusted under 35 U.S.C. 154(b) by 474 days.

(21) Appl. No.: 10/800,898

(22) Filed: Mar. 15, 2004

(65) Prior Publication Data

US 2004/0204434 A1    Oct. 14, 2004

Related U.S. Application Data

(60) Provisional application No. 60/454,253, filed on Mar. 13, 2003.

(51) Int. Cl.
*A61K 31/485* (2006.01)
*C07D 489/02* (2006.01)

(52) U.S. Cl. ........................... 514/282; 546/46; 546/44
(58) Field of Classification Search ................ 514/282; 546/44, 46
See application file for complete search history.

(56) References Cited

U.S. PATENT DOCUMENTS

| | | | |
|---|---|---|---|
| 3,299,072 | A | 1/1967 | Bartels-Keith |
| 3,966,940 | A | 6/1976 | Pachter et al. |
| 4,457,933 | A | 7/1984 | Gordon et al. |
| 4,489,065 | A | 12/1984 | Walton et al. |
| 4,661,492 | A | 4/1987 | Lewis et al. |
| 4,769,372 | A | 9/1988 | Kreek |
| 4,785,000 | A | 11/1988 | Kreek et al. |
| 5,130,126 | A | 7/1992 | Koyama et al. |
| 5,149,538 | A | 9/1992 | Granger et al. |
| 5,176,907 | A | 1/1993 | Leong |
| 5,194,581 | A | 3/1993 | Leong |
| 5,236,714 | A | 8/1993 | Lee et al. |
| 6,051,576 | A | 4/2000 | Ashton et al. |
| 6,228,863 | B1 | 5/2001 | Palermo et al. |
| 6,277,384 | B1 | 8/2001 | Kaiko et al. |
| 6,375,957 | B1 | 4/2002 | Kaiko et al. |
| 6,451,806 | B2 | 9/2002 | Farrar |
| 6,475,494 | B2 | 11/2002 | Kaiko et al. |
| 2003/0022876 | A1 | 1/2003 | Ashton et al. |
| 2004/0058946 | A1 | 3/2004 | Buchwald et al. |

FOREIGN PATENT DOCUMENTS

| EP | 1 258 246 | 11/2002 |
|---|---|---|
| GB | 1 300 419 | 12/1972 |
| WO | WO 02/094254 A2 | 11/2002 |
| WO | WO 03/072046 * | 9/2003 |

OTHER PUBLICATIONS

Agarwal, V. and Mishra, B.; "Design, Development, and Biopharmaceutical Properties of Buccoadhesive Compacts of Pentazocine;" *Drug Dev. Ind. Pharm;* Jun. 1999; 25 (6); 701-709.
Buckett, W. R.; "The Relationship Between Analgesic Activity, Acute Toxicity and Chemical Structure Inesters of 14-Hydroxycodeinone;" *J Pharm Pharmacol;* Dec. 1964; 16 Suppl-71T.
Buckett, W. R; Farquharson, M. E.; and Haining, C. G.; "The Analgesic Properties of Some 14-Substituted Derivatives of Codeine and Codeinone;" *J Pharm Pharmacol;* Mar. 1964; 16 174-182.
Okuda, T.; Tsuchiya, N.; Wakita, K.; Hatsuoka, K.; Koga, Y.; Ueda, S.; and Kaetsu, I.; "[Prolonged Antinociceptive Effect After Epidural Injection of Polyethylene Glycol-Morphine Composites in Rats];" *Masui;* May 1996; 45 (5); 571-575.
Nagase et al.; "The Facility of Formation of a $\Delta^6$ Bond in Dihydromorphinone and Related Opiates;" *J. Org. Chem.;* 1989, vol. 54; 4120-4125.
Hansen, H. C. and Spillum, A.; "Loss of Nitroglycerin During Passage Through Two Different Infusion Sets;" *Acta Pharm Nord.;* 1991; 3 (3); 131-136.
Hosztafi, S.; Kohegyi, I.; Simon, C.; and Furst, Z.; "Synthesis and Analgetic Activity of Nicotinic Esters of Morphine Derivatives;" *Arzneimittelforschung.;* Nov. 1993; 43 (11); 1200-1203.
Hussain, M. A.; Aungst, B. J.; Koval, C. A.; and Shefter, E.; "Improved Buccal Delivery of Opioid Analgesics and Antagonists With Bitterless Prodrugs:" *Pharm Res;* Sep. 1988; 5 (9); 615-618.
Stinchcomb, A. L.; Paliwal, A.; Dua, R.; Imoto, H.; Woodard, R. W.; and Flynn, G. L.; "Permeation of Buprenorphine and Its 3-Alkyl-Ester Prodrugs Through Human Skin;" *Pharm Res;* Oct. 1996; 13 (10); 1519-1523.
Stinchcomb, A. L.; Swaan, P. W.; Ekabo, O.; Harris, K. K.; Browe, J.; Hammell, D. C.; Cooperman, T. A.; and Pearsall, M.; "Straight-Chain Naltrexone Ester Prodrugs: Diffusion and Concurrent Esterase Biotransformation in Human Skin;" *J Pharm Sci;* Dec. 2002; 91 (12); 2571-2578.

* cited by examiner

*Primary Examiner*—Charanjit S. Aulakh
(74) *Attorney, Agent, or Firm*—Peter J. Knudsen

(57) ABSTRACT

The abuse potential of a bioavailable drug such as an opiate analgesic agent is reduced and its duration of action is extended by converting it to a poorly absorbed ester prodrug or other prodrug derivative prior to formulation. Unlike many existing sustained release formulations of active pharmaceutical agents wherein an active pharmaceutical agent can be released by chewing, crushing, or otherwise breaking tablets or capsule beads containing the active pharmaceutical agent, such mechanical processing of tablets or capsule beads containing a prodrug of this invention neither releases the active drug nor compromises the controlled conversion of prodrug to drug. Moreover, tablets and capsule beads containing prodrugs of this invention or other drugs can be formulated with a sufficient amount of a thickening agent such as hydroxypropylmethylcellulose or carboxymethylcellulose to impede inappropriate intravenous and nasal administration of formulations that are not indicated for these modes of administration.

17 Claims, No Drawings

COMPOUNDS AND METHODS FOR LOWERING THE ABUSE POTENTIAL AND EXTENDING THE DURATION OF ACTION OF A DRUG

This claims priority under 35 U.S.C. §119(e) to U.S. Provisional Application No. 60/454,253 filed Mar. 13, 2003; the entire contents of which are incorporated herein by reference

BACKGROUND OF THE INVENTION

The duration of action of orally administered drugs in tablets or capsules is often extended by utilizing a controlled release method of delivery wherein an active pharmaceutical agent is coated and/or encapsulated and/or otherwise entrapped by a material that delays dissolution of the active agent. This method of delivery requires a larger amount of active agent than immediate release formulations to allow for a longer duration of action. Intentional or unintentional mechanical processing of such controlled release tablets or capsule beads could compromise the controlled release action of such formulations, and thereby may produce, subsequent to administration, toxic levels of active drug. Thus, for example, controlled release morphine marketed under the name Avinza® and controlled release oxycodone marketed under the name OxyContin® contain sufficient opioid to produce powerful euphoria as well as potentially fatal respiratory depression when controlled release tablets or capsule beads are chewed, crushed, ground, or otherwise broken so as to compromise the controlled release action of the formulation as indicated by the black box warning on the package insert for OxyContin® and Avinza®).

Because one can easily achieve a powerful morphine-like high after oral intravenous or nasal administration of crushed tablets or capsule beads, the abuse potential of these formulations is great. Consequently, abuse of OxyContin® has become a serious problem as evidenced by medical examiner reports that attribute several hundred deaths per year to abuse of sustained release oxycodone, and as evidenced by the substantial fraction of new enrollees in methadone treatment centers who indicate sustained release oxycodone as their primary drug of abuse.

Numerous U.S. Publications (e.g. U.S. Pat. Nos. 6,475,494; 6,451,806; 6,375,957; 6,277,384; 6,228,863; 4,785,000; 4,769,372; 4,661,492; 4,457,933; and 3,966,940) describe the addition of an opioid antagonist such as naloxone or naltrexone to formulations of opioid agonists for purposes of lowering their abuse potential. Typically this approach relies on the use of a form and/or amount of antagonist that is able to neutralize the opioid agonist when the contents of crushed tablets are administered parenterally, but not when unbroken tablets are administered orally as medically indicated. An oral formulation of the opioid pentazocine marketed under the name TALWIN® Nx contains naloxone to impede abusive intravenous administration. Abusive intravenous administration of TALWIN Nx, however, may cause harmful withdrawal syndromes in narcotic dependent individuals. Although Talwin Nx has a lower potential for abusive parenteral administration than previously marketed oral pentazocine formulations containing no antagonist, it still is subject to abusive oral administration. U.S. Pat. Nos. 5,149,538 and 5,236,714 discuss the use of antagonists to impede abuse of opioid formulations that are medically indicated for transdermal administration. U.S. Pat. Nos. 4,457,933 and 6,475,494 disclose that the presence of an appropriate amount of an opioid antagonist in an agonist formulation medically indicated for oral administration may also reduce abusive oral administration of that formulation. This reduction has been attributed (U.S. Pat. No. 6,475,494) to an aversive effect of the antagonist in physically dependent individuals. WO 02094254 describes addition of an appropriate amount of capsaicin to an oral formulation to deter abusers from crushing prescription pharmaceutical tablets for abusive snorting, injection or ingestion.

Other side effects of opioid analgesics include gastrointestinal dysfunction caused by the opioids binding to the $\mu$ receptors present in the gastrointestinal tract. The side-effects in the stomach include a reduction in the secretion of hydrochloric acid, decreased gastric motility, thus prolonging gastric emptying time, which can result in esophageal reflux. Passage of the gastric contents through the duodenum may be delayed by as much as 12 hours, and the absorption of orally administered drugs is retarded. In the small intestines the opioid analgesics diminish biliary, pancreatic and intestinal secretions and delay digestion of food in the small intestine. Resting tone is increased and periodic spasms are observed. The amplitude of the nonpropulsive type of rhythmic, segmental contractions is enhanced, but propulsive contractions are markedly decreased. Water is absorbed more completely because of the delayed passage of bowel contents, and intestinal secretion is decreased increasing the viscosity of the bowel contents. Propulsive peristaltic waves in the colon are diminished or abolished after administration of opioids, and tone is increased to the point of spasm. The resulting delay in the passage of bowel contents causes considerable desiccation of the feces, which, in turn retards their advance through the colon. The amplitude of the non-propulsive type of rhythmic contractions of the colon usually is enhanced. The tone of the anal sphincter is greatly augmented, and reflex relaxation in response to rectal distension is reduced. These actions, combined with inattention to the normal sensory stimuli for defecation reflex due to the central actions of the drug, contribute to opioid-induced constipation.

Although addition of opioid antagonists and other aversive agents to pharmaceutical tablets or capsules may well prevent abuse, they may also do harm. Thus, there is a need for the developments of a new class of opioid analgesics that are abuse resistant and have lower propensity to agonize the $\mu$ receptors in the gastrointestinal tract than the opioid analgesics present in the prior art.

SUMMARY OF THE INVENTION

The present invention fills this need by providing for a method for producing non-naturally occurring prodrugs of analgesic drugs that bind to $\mu$ opioid receptors that has a low abuse potential, an extended duration of action and reduced GI side-effects. Also claimed are prodrugs of analgesic drugs that have lower binding affinity to $\mu$ opioid receptors than the analgesic drug. The method of this invention involves converting, prior to formulation, a bioavailable analgesic drug that binds to a $\mu$ opioid receptor to a prodrug that limits the accessibility of the drug to its target tissue. Unlike many existing sustained release tablet and capsule formulations of active pharmaceutical agents wherein the active pharmaceutical agent can be released by chewing, crushing, or otherwise breaking tablets or capsule beads containing the active pharmaceutical agent, such mechanical processing of tablet or capsule formulations of prodrugs of this invention neither releases the agent nor compromises the conversion of inactive prodrug to active drug.

The prodrug compositions of this invention limit the bioavailability of the drug, because the prodrug is poorly absorbed by the blood after administration by the medically indicated route of administration or in cases wherein the prodrug is absorbed by the blood or in cases wherein the prodrug is injected directly into the blood stream the prodrug is more poorly absorbed by or has a smaller therapeutic effect on the target tissue than the drug.

This invention includes but is not limited to ester prodrug compositions of bioavailable opioid analgesic agents wherein an alkyl or cyclic alkyl, or phenolic or enolic hydroxyl group of the drug is covalently linked to an acyl group, and wherein the acyl group is chosen so as to limit the bioavailability of and rate of conversion of prodrug to drug so as to produce the desired duration of action of the drug.

Also included in this invention is a method involving the use of a thickening agent such as hydroxypropylmethylcellulose or carboxymethylcellulose to impede intranasal or intravenous administration of formulations of the prodrugs of this invention or other formulations of medications that are not medically indicated for intranasal or intravenous administration.

DETAILED DESCRIPTION OF THE INVENTION

Definitions:

Receptor Binding Affinity is the binding strength that a molecule has to a receptor. Affinity is measured by the equilibrium dissociation constant of the drug-receptor complex (denoted $K_d$); the fraction of receptors occupied by the drug is determined by the concentration of drug and $K_d$. See Goodman & Gilman's "*The Pharmacological Basis of Therapeutics*" 10ed. (2001) pages 39–40 (McGraw-Hill, New York, N.Y.).

μ Opioid Receptor is the primary receptor to which the opioid analgesic drugs bind to produce their analgesic effects. The opioid analgesic drugs are morphine-related drugs. Examples of opioid analgesics include morphine, hydromorphone, oxymorphone, levorphanol, levallorphan codeine, hydrocodone and oxycodone. Another class of analgesic drugs that bind to the μ opioid receptor is the piperidine and phenylpiperidine class of analgesics such as meperidine, diphenoxylate, loperamide, fentanyl, sufentanil, alfentanil, and remifentanil.

Included in this invention is a method for producing pharmaceutical agents with both a low abuse potential and an extended duration of action. The method involves conversion, prior to formulation, of a bioavailable analgesic drug to a prodrug that is more poorly absorbed by and/or more poorly activates the target tissue. This invention includes but is not limited to ester prodrug compositions of bioavailable opioid analgesic agents wherein an alkyl or cyclic alkyl or phenolic or enolic hydroxyl group of the drug is covalently linked to an acyl group that has the following structure

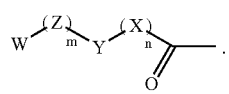

I wherein the values of m and n are independently selected from the values 0, 1, 2 or 3

Z and X are independently selected from

and W is selected from $R_1$.

wherein, $R_1$, $R_2$, and $R_3$ are independently selected from
hydrogen.
$C_{1-4}$ alkyl unsubstituted or substituted with $CH_3$ or $C_{3-7}$ cycloalkyl, or amino or guanidino or amidino or carboxy or acetamido or carbamyl or sulfonate, phosphate or phosphonate.
$C_{1-4}$ alkoxy.
methylenedioxy.
hydroxy.
carboxy.
sulfonate.
$C_{3-7}$ cycloalkyl.
aryl unsubstituted or substituted with guanidino or amidino or carboxy or acetamido or carbamyl or sulfonate, phosphate or phosphonate.
benzyl with the benzene ring unsubstituted or substituted with guanidino or amidino or carboxy or acetamido or carbamyl or sulfonate, phosphate or phosphonate.
$R_1$ and $R_2$ along with the carbon or carbon atoms to which they are attached form a $C_{3-7}$ cycloalkyl ring

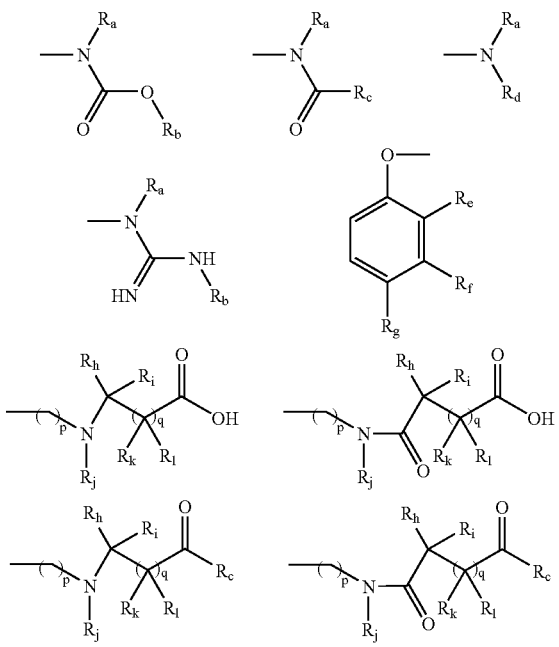

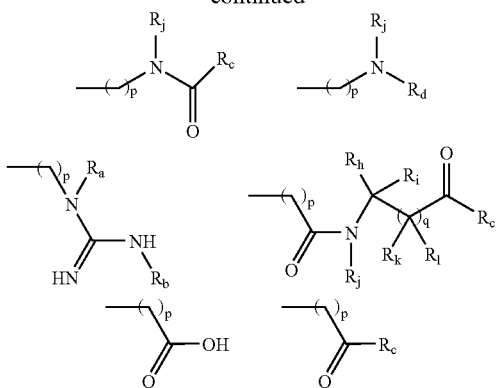

wherein $R_a$ and $R_b$ are independently selected from hydrogen.
$C_{1-4}$ alkyl unsubstituted or substituted with $CH_3$ or $C_{3-7}$ cycloalkyl.
$C_{3-7}$ cycloalkyl.
aryl unsubstituted or substituted with guanidino or amidino or carboxy or acetamido or carbamyl or sulfonate, phosphate or phosphonate.
benzyl with the benzene ring unsubstituted or substituted with guanidino or amidino or carboxy or acetamido or carbamyl or sulfonate, phosphate or phosphonate.

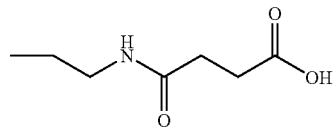

wherein $R_c$ is selected from hydrogen.
$C_{1-4}$ alkyl unsubstituted or substituted with $CH_3$ or $C_{3-7}$ cycloalkyl, or amino or guanidino or amidino or carboxy or acetamido or carbamyl or sulfonate, phosphate or phosphonate.
aryl unsubstituted or substituted with guanidino or amidino or carboxy or acetamido or carbamyl or sulfonate, phosphate or phosphonate.
benzyl with the benzene ring unsubstituted or substituted with guanidino or amidino or carboxy or acetamido or carbamyl or sulfonate, phosphate or phosphonate.
cellulose or a cellulose derivative such as methyl cellulose, hydroxyethylcellulose or hydroxypropylcellulose such that one or more hydroxyl groups in the cellulose or cellulose derivative forms an ester or urethane linkage in the prodrug.
poly(ethylene glycol) or a poly(ethylene glycol) derivative such as poly(ethylene glycol) methyl ether, poly(ethylene glycol) ethyl ether, poly(ethylene glycol) carboxymethyl ether, poly(ethylene glycol) monolaurate such that one or more of the hydroxyl groups of the poly(ethylene glycol) or the poly(ethylene glycol) derivative form ester or urethane linkage in the prodrug.
wherein $R_d$ is selected from
a polycarboxylic acid such as carboxymethylcellulose or a derivative thereof, polyacrylic acid or a derivative thereof, polymethacrylic acid or a derivative thereof such that one or more of the carboxyl groups of the macromolecule forms an amide linkage in the prodrug.
poly(ethylene glycol) bis(carboxymethyl) ether, or poly(ethylene glycol) carboxymethyl, methyl ether or similar carboxylic acid containing poly(ethylene glycol) derivative such that one or more carboxyl groups of the poly(ethylene glycol) derivative forms an amide linkage in the prodrug.
wherein $R_e$, $R_f$ and $R_g$ are independently selected from hydrogen.

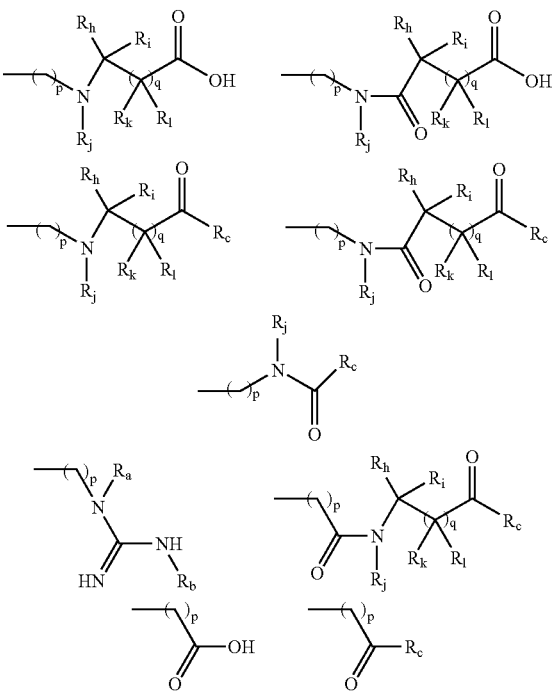

wherein the values of p, and q are independently selected from the values 0, 1, 2, or 3
wherein $R_h$, $R_i$, $R_k$ and $R_l$ are independently selected from hydrogen.
$C_{1-4}$ alkyl unsubstituted or substituted with $CH_3$ or $C_{3-7}$ cycloalkyl, or amino or guanidino or amidino or carboxy or acetamido or carbamyl or sulfonate, phosphate or phosphonate.
aryl unsubstituted or substituted with a guanidino or amidino or carboxy or acetamido or carbamyl or sulfonate, phosphate or phosphonate.
benzyl with the benzene ring unsubstituted or substituted with a guanidino or amidino or carboxy or acetamido or carbamyl or sulfonate, phosphate or phosphonate $R_h$ and $R_i$ along with the carbon to which they are attached form a $C_{3-7}$ alkyl ring.
$R_k$ and $R_l$ along with the carbon to which they are attached form a $C_{3-7}$ alkyl ring,
wherein $R_j$ is selected from hydrogen.
$C_{1-4}$ alkyl unsubstituted or substituted with $CH_3$ or $C_{3-7}$ cycloalkyl.
$C_{3-7}$ cycloalkyl.
Aryl unsubstituted or substituted with a carboxyl or guanidino or amidino or carboxy or acetamido or carbamyl or sulfonate, phosphate or phosphonate.

benzyl with the benzene ring unsubstituted or substituted with a guanidino or amidino or carboxy or acetamido or carbamyl or sulfonate, phosphate or phosphonate.

a polycarboxylic acid such as carboxymethylcellulose or a derivative thereof, polyacrylic acid or a derivative thereof, polymethacrylic acid or a derivative thereof such that one or more carboxyl groups in the macromolecule forms an amide linkage in the prodrug.

poly(ethylene glycol) bis(carboxymethyl) ether, or poly(ethylene glycol) carboxymethyl, methyl ether or similar carboxylic acid containing poly(ethylene glycol) derivative such that one or more carboxyl groups of the poly(ethylene glycol) derivative forms an amide linkage in the prodrug.

Y is independently selected from the following

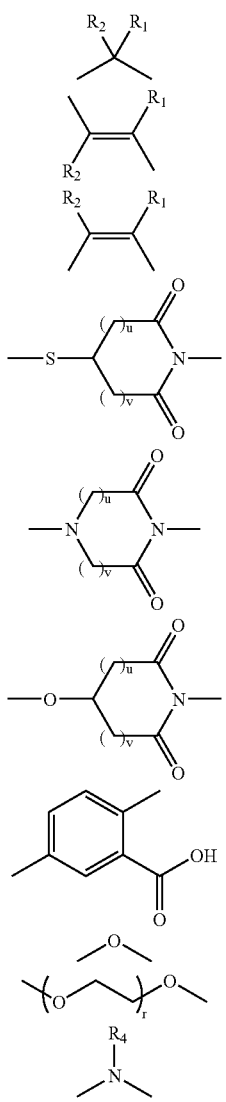

wherein the values of u and v are independently selected from the values 0, 1, 2 or 3, and the value of r is a value between 10 and 1,000.

wherein $R_4$ is independently selected from $R_a$.

$R_b$.

$R_d$.

The compounds of the invention may have chiral centers and may occur as epimeric mixtures, diastereomers, and enantiomers. All such stereoisomers are included in this invention. When any variable occurs repeatedly in formula I, the definition of that variable is independent of its definition at every other occurrence of that variable. Additionally, combinations of variables and substituents are permissible only when they produce stable compounds.

Some of the abbreviations that may appear in this application are as follows:

| Designation | Definition |
|---|---|
| Boc | tert-butyloxycarbonyl |
| tBu | tert-butyl |
| Cbz | benzyloxycarbonyl |
| DCM | dichloromethane |
| DCC | N,N'-dicyclohexylcarbodiimide |
| DCU | N,N'-dicyclohexylurea |
| DIEA | diisopropylethylamine |
| DMAP | 4-(dimethylamino)pyridine |
| EtOAc | ethyl acetate |
| Glu | glutamic acid |
| h | hour(s) |
| HOBt | 1-hydroxybenzotriazole |
| HPLC | high performance liquid chromatography |
| min | minute(s) |
| NMR | nuclear magnetic resonance |
| rt | room temperature |
| TEA | triethylamine |
| TFA | trifluoroacetic acid |
| THF | tetrahydrofuran |
| TLC | thin layer chromatography |

The acyl portion of the prodrug ester is chosen so as to endow the prodrug with i) a low bioavailability and ii) a rate of conversion of prodrug to drug that results in a desired oscillation in the plasma concentration of drug over the dosing interval.

To restrict entry of the prodrug into the blood and/or entry of the prodrug into the central nervous system or otherwise restrict the bioavailability of the prodrug, one chooses a macromolecular acyl group ($M_r$ greater than about 1000), and/or a low molecular weight acyl group ($M_r$ less than about 1000) that contains one or more groups that bear a charge at pH 7, and/or groups that contain multiple hydrogen bond donors and acceptors such as amide groups.

In cases wherein the prodrug is poorly absorbed into the blood stream after administration, the rate of conversion of prodrug to drug substantially controls the duration and intensity of the effect of the drug. In cases wherein the prodrug is directly injected into the blood or it is absorbed into the blood, but does not enter or activate the target tissue, the effect of administration of the prodrug also will be controlled substantially by the rate of conversion of prodrug to drug.

We have discovered how to produce ester prodrugs of alkaloid opioid analgesics with rates of nonenzymatic hydrolysis at pH 7 compatible with a wide range of dosing frequencies. It is recognized that for some of the prodrugs included in this invention, enzymes may contribute to the rate of conversion of prodrug to drug. The contribution of such enzymatically catalyzed conversions to the overall rate of conversion of prodrug to drug may be roughly estimated from in vitro assessment of the conversion of the drug in presence of digestive enzymes and blood plasma. Comparative pharmacokinetic studies after administration of drug and prodrug to a patient should yield an accurate estimate of the time dependent conversion of prodrug to drug in the patient. When desirable it should be possible for someone skilled in the art to adjust the rate of nonenzymatic conversion and enzymatically catalyzed conversion of prodrug to drug by judicious modification of the structure of the prodrug. Moreover, someone skilled in the art should be able to formulate combinations of prodrug derivatives that release the same drug at differents rates so as to produce a desired oscillation in plasma drug concentration over the dosing interval.

The feasibility of forming enol esters of alkaloid opioids related to dihydromorphinone has been demonstrated by Nagase et al. and by Hosztafi et al. These investigators, however, studied neither the hydrolysis of opioid enol esters nor their suitability as prodrugs.

Esters of the phenolic hydroxyl group of various opioid agonists and antagonists have been studied as prodrugs for increasing the efficiency of transdermal, sublingual and buccal delivery and masking the bitter taste opioid agonists and antagonists (see for example, Hansen et al. Stinchcomb et al. and Hussain et al.)

For enol esters and phenyl esters wherein the alcohol portion of the ester is a good leaving group the rate of ester hydrolysis is increased by increasing the acidity of the carboxyl group of parent carboxylic acid and/or by utilizing an acyl group that contains an appropriate neighboring nucleophilic catalyst such as a carboxylate group that is capable of facilitating hydrolysis via nucleophilic catalysis as exemplified below. In cases wherein the intrinsic rate of hydrolysis at pH 7 is more rapid than desired, steric and charge effects can be employed to reduce the rate of hydrolysis at pH 7 as exemplified below.

Listed below by way of example and without limitation are some oxycodone prodrug compositions included in this invention that have an acyl group with structure I.

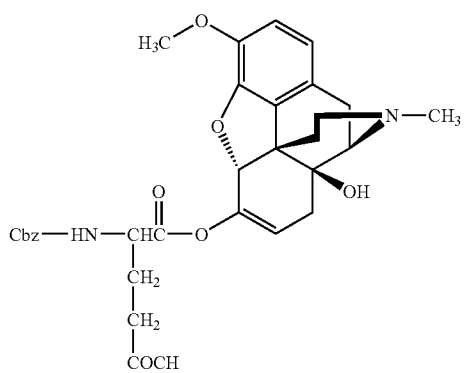

1

-continued

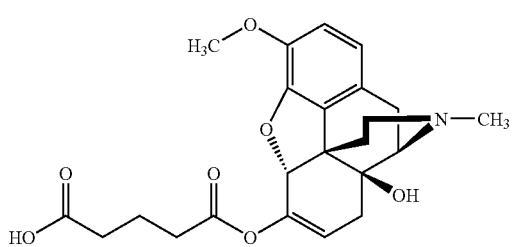

2

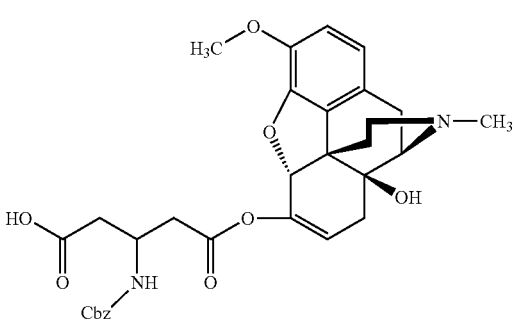

3

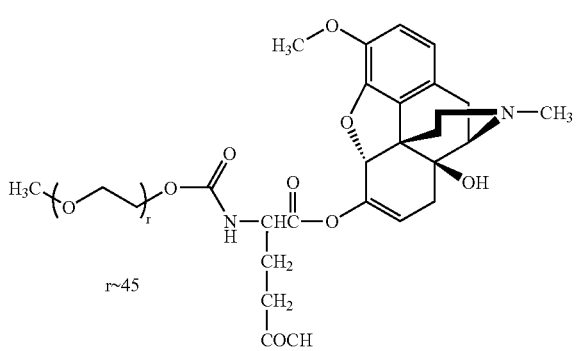

4

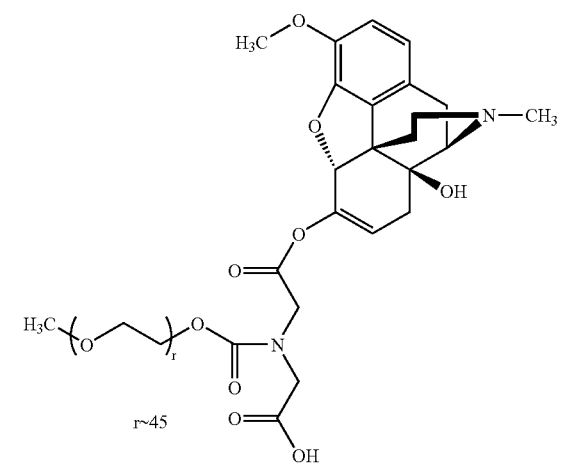

5

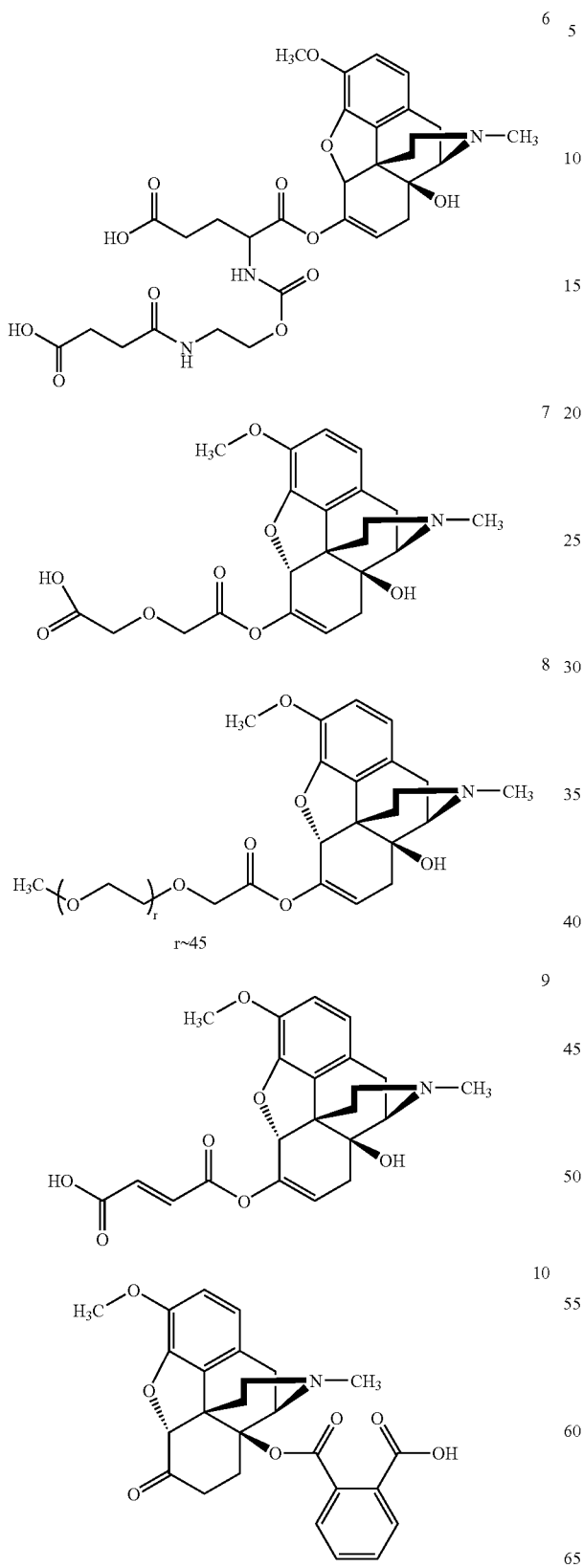

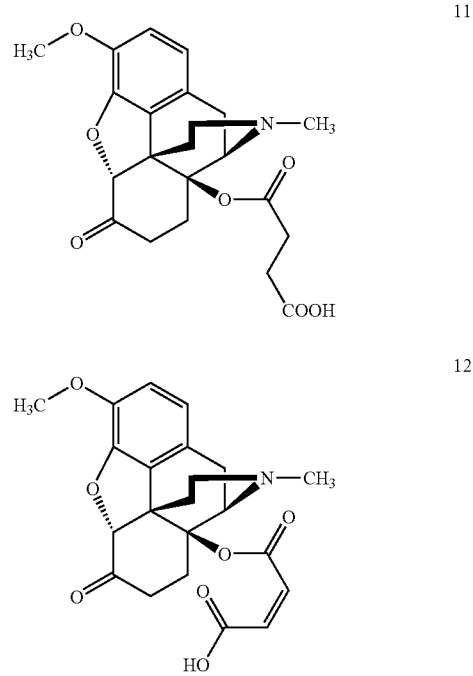

The zwitterionic character and/or molecular weight of these compounds endow them with a low bioavailability, relative to that of the drug.

Enol ester prodrugs 1–7 are carboxylic acid derivatives, wherein the free carboxylate (at pH 7) group facilitates hydrolysis of the enol ester and endows the enol ester with a rate of hydrolysis that changes little in the pH range 6–8. This effect minimizes intra-individual (over time) or inter-individual variation in the rate of hydrolysis of compounds 1–7 due to variation of the pH within the intestinal lumen. It is important to note that the disposition of the carboxylate group is an important determinant of the rate of hydrolysis of it effect on ester hydrolysis (see Table I).

TABLE I

Half-Life for the Nonenzymatic Hydrolysis of Oxycodone Enol Ester Prodrugs at pH 7.0, 37° C.*

| R— | Half life* (h) |
|---|---|
| (structure with OH, O, O-) | <0.5 |

TABLE I-continued

Half-Life for the Nonenzymatic Hydrolysis of Oxycodone Enol Ester Prodrugs at pH 7.0, 37° C.*

[Oxycodone enol ester core structure with R substituent at 6-position, 14-OH, N-CH3, and 3-methoxy groups]

| R— | Half life* (h) |
|---|---|
| HOOC–CH2–CH2–C(=O)–O— (succinate mono-ester) | 11.4 |
| HOOC–CH2–CH(CH3)–C(=O)–O— (methylsuccinate) | 3.5 |
| HOOC–CH2–CH(NHCbz)–C(=O)–O— (Cbz-glutamate) | 6.5 |
| HOOC–CH2–O–CH2–C(=O)–O— (diglycolate) | 2.4 |
| HOOC–(CH2)3–C(=O)–O— (glutarate) | 173 |
| HOOC–CH=CH–C(=O)–O— (fumarate) | 66 |
| H3C–(O–CH2CH2)r–O–C(=O)–NH–CH(CH2CH2COOH)–C(=O)–O—, r~45 | 6.4 |
| H3C–(O–CH2CH2)r–O–C(=O)–N(CH2COOH)–CH2–C(=O)–O—, r~45 | 11.3 |
| H3C–(O–CH2CH2)r–O–C(=O)–NH–CH2–C(=O)–O—, r~45 | 6.9 |

*Half-life was determined from the first order conversion of prodrug to oxycodone in buffered solution maintained at 37° C. The amount of prodrug remaining was determined by HPLC wherein the ester was quantified from measurements of the area under the prodrug peak in chromatograms wherein the absorbance of the ester (typically at 280 nm) was monitored using a diode array detector. Plots of the logarithm of the fraction of prodrug remaining versus time were linear as expected for a first order process.

It is important to note that the hydrolysis of alkyl esters with higher pK alcohol leaving groups (such as esters 10–12) is not facilitated by the presence of a neighboring carboxyl group (See Table II). We observed, however, that esters of the 14-hydroxyl group in oxycodone are hydrolyzed rapidly at pH 7. For example we found that the half-life for the hydrolysis of the 14-acetate ester of oxycodone is ~20 min at pH 7, 37° C., whereas the half-life for hydrolysis of the 6-enolacetate is ~4 days under these conditions. The high rate of hydrolysis of the oxycodone 14-acetate may well reflect intramolecular nucleophilic attack by the neighboring tertiary amino group in oxycodone to form an acylammonium ion intermediate that is rapidly hydrolyzed at pH 7.

TABLE II

Half-Life for the Nonenzymatic Hydrolysis of Oxycodone 14-Ester Prodrugs at pH 7.0, 37° C.*

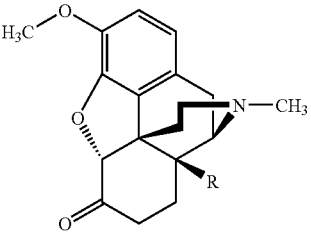

| | R — | | |
|---|---|---|---|
| Half life (h) | 7.0 | 2.1 | 1.9 |

*Half-Life was determined as described in Table I.

Included in this invention is a method to impede intravenous and nasal administration of hydrolytically treated prodrug tablets or capsule beads by formulating the prodrugs with an appropriate amount of a thickening agent such as hydroxypropylmethylcellulose or carboxymethylcellulose. Hydrolytic treatment of such ester prodrug formulations to release the drug produces a high viscosity glue-like material that would be difficult to administer nasally. Moreover, this material requires dilution to more than 10 mL to easily pass through a hypodermic needle suitable for intravenous administration. Also included in this invention is a method to add a sufficient amount of a thickening agent such as hydroxypropylmethylcellulose or carboxymethylcellulose to impede intravenous and nasal administration of drug and prodrug formulations that are not indicated for these routes of administration. Dissolution for intravenous administration of a drug or prodrug in a formulation containing the thickening agent produces a highly viscous glue-like material that requires dilution to more than 10 mL to easily pass through a hypodermic needle suitable for intravenous administration. The thickening agent also reduces absorption of drug or prodrug from nasally administered powdered tablets or capsule beads. This reduction may reflect an osmotic effect of the thickening agent.

Ester prodrugs of the invention can be prepared according to the general procedures outlined below:

General Procedure for the Preparation of Enol Ester Prodrugs.

The free base form of an aldehyde or ketone containing drug at 0.0.025–0.5 mol/L is dissolved or suspended in an aprotic polar solvent such as anhydrous THF or DCM under argon and cooled in a acetone/dry-ice bath. A 1.05 molar excess over drug of potassium tBu-OH is added, and the reaction mixture stirred for 40 min. A 1.0–1.2 molar excess over drug of the nitrophenyl ester of the carboxylic acid to be esterified by the enol group of the drug is added via syringe as a 0.025–2.0 M. solution in THF or DCM. After 1–2 h, or when the reaction is complete as judged by formation of the enol ester and liberation of nitrophenol, the reaction is neutralized by the addition of TFA. If the reaction solidifies at −78° C., it is allowed to warm to rt before addition of the TFA. In cases involving the formation of hemi-esters of certain symmetrical dicarboxylic acids, one can use the cyclic dicarboxylic acid anhydride in place of a nitrophenyl ester.

The Following Carbodiimide Mediated Coupling Reactions can also be Used to Prepare Enol Ester Prodrugs.

The free base form of an aldehyde or ketone containing drug at a concentration of 0.025–1.0 M in an aprotic polar solvent such as anhydrous acetonitrile, THF, or DCM is treated with a 3–6-fold molar excess of a tertiary amine strong base such as TEA or DIEA for 20–30 min at rt to promote enolate formation. DMAP, DCC, and carboxylic acid are then added so that the molar ratio DMAP: carboxylic is in the range of 0.5–1.0, the molar ratio DCC:carboxylic acid is in the range 0.5–1.5, and the molar ratio of carboxylic acid:drug is in the range 2–6.

In cases wherein a low yield is obtained using this procedure, addition, prior to addition of carboxylic acid, of HOBt (in a molar amount approximately equivalent to the carboxylic acid) may increase the yield. Groups in the prodrug that might interfere with ester formation can be blocked with groups (such as Boc, tBu, and Cbz) that may be removed after ester formation without significant decomposition of the ester.

General Procedure for the Preparation of Alcohol Ester and Phenyl Ester Prodrugs.

The above procedure for preparation of enol esters wherein the addition of strong base (to promote enolization) is eliminated may also be used to prepare alcohol and phenyl ester prodrugs. Additionally, alcohol ester prodrug may be prepared by condensing cyclic carboxylic acid anhydrides with drugs containing an alkyl or cycloalkyl hydroxyl group in pyridine as described in EXAMPLE 2. It is important to note that i) dicarboxylic acids (such as maleic acid, phthalic acid and succinic acid) that facilely form cyclic anhydrides form unstable phenyl and enol esters; ii) esters of the 14-hydroxyl group of drugs in the 14-hydroxymorphinan family that contain a tertiary 17-amino group are unstable unless hydroxide ion catalyzed ester hydrolysis is electrostatically or sterically impeded; iii) enol ester formation can be eliminated by forming acid labile ketal and acetal derivatives of drugs that contain these groups. One skilled in the art can exploit these findings together with differential chromatographic properties to convert a drug containing more than one hydroxyl group to a desired mono ester prodrug.

EXAMPLE 1

Preparation of Pentanedioic Acid Mono-(3-methoxy-14-hydroxy-6,7-didehydro-4,5α-epoxy-17-methylmorphinan-6-yl) ester (1-4, Also Designated Compound 2)

Step A: Preparation of Oxycodone Free Base (1-1)

Oxycodone (1 g) was dissolved in water (5 mL) and mixed with 30 mL of a saturated sodium bicarbonate solution to produce the free base. The resulting suspension was extracted with three 70 mL portions of EtOAc. The combined EtOAc extract was washed with 30 mL of saturated sodium bicarbonate, 30 mL of brine and dried over magnesium sulfate. EtOAc was removed under reduced pressure from the resulting solution to yield 785 mg of oxycodone free base.

Step B: Preparation of Pentanedioic Acid Mono-Tert-Butyl Ester (1-2)

Potassium tert-butoxide (2.7 g, 24 mmol) was dissolved in 17 mL of anhydrous THF at rt. After 5 min glutaric anhydride (2.4 g, 21 mmol) was added and the resulting suspension stirred for 2 h at rt. The reaction mixture was then quenched with 20 mL of 1 M $KHSO_4$, extracted with 50 mL of EtOAc, adjusted to pH 2–3 with 1 M $KHSO_4$ and extracted twice with 50 mL EtOAc. The combined extracts were dried over anhydrous magnesium sulfate, filtered and concentrated to give a yellow oil which was purified by silica gel flash chromatography (eluent: EtOAc:Hexanes- 1:1) to give 1.65 g (35% yield) pure (TLC) 1-2.

Step C: Preparation of Pentanedioic Acid tert-butyl ester 3-methoxy-14-hydroxy-6,7-didehydro-4,5α-epoxy-17-methylmorphinan-6-yl ester (1-3)

A suspension of oxycodone free base (100 mg, 0.317 mmol) in 1.5 mL of anhydrous acetonitrile was stirred for 20 min with DIEA (0.2 mL 1.15 mmol). DMAP (63 mg, 0.516 mmol) and DCC (112 mg, 0.545 mmol) were then added to the stirred suspension. After 5 min 1-2 (150 mg, 0.8 mmol) was added, the mixture stirred for 16 h at rt, and the resulting orange suspension concentrated to an oil under reduced pressure. The concentrated mixture was stirred with 6 mL of acetone for 10 min, and the precipitated DCU removed by filtration. The filtrate was concentrated to give a brown oil. HPLC analysis of the oil indicated that the primary reaction product was 1-3. The concentrated oil was subjected to reverse phase C-18 silica gel chromatography using a gradient of 25–40% acetonitrile in 0.07% aqueous TFA as eluent. Evaporation of the eluent from the fraction containing 1-3 gave 82 mg (53% yield) of a colorless oil which was greater than >99% pure 1-3 (HPLC).

Step D: Preparation of Pentanedioic Acid Mono-(3-methoxy-14-hydroxy-6,7-didehydro-4,5α-epoxy-17-methylmorphinan-6-yl) ester (1-4)

1-3 was treated with 0.5 mL of TFA and after 15 min at rt, the TFA was removed under reduced pressure to yield >98% pure 1-4 as indicated by HPLC and the $^1$H and $^{13}$C NMR spectra. (As expected for enol ester 1-4, the $^1$H NMR spectrum of the product exhibited a resonance for a vinylic proton at $C_7$ at 5.53 ppm and the $^{13}$C NMR spectrum of the product exhibited no resonance for a ketonic carbonyl carbon atom in the region of 207 ppm.)

EXAMPLE 2

Preparation of Phthalic Acid Mono-(3-methoxy-4, 5α-epoxy-17-methylmorphinan-6-one-14-yl) ester (2-1, also designated compound 10)

A solution comprised of oxycodone free base, 1-1, (63 mg, 0.2 mmol), phthalic anhydride (1.185 g, 8.0 mmol) and DMAP (24 mg, 0.2 mmol) in 10 mL of pyridine was stirred in an oil bath at 50–55° C. for 24 h and concentrated under reduced pressure. The residue was subjected to silica gel flash chromatography with a 5%–20% methanol in dichloromethane gradient. The fraction containing 2-1 was collected and concentrated under reduced pressure. HPLC indicated that the fraction was 60% pure. The concentrated fraction was subjected to another silica gel flash chromatography using a gradient of 0–20% methanol in dichloromethane as eluent to yield a fraction containing 32 mg (35% yield) of 96% pure (HPLC) 2-1, which was further purified by HPLC. The $^1$H and $^{13}$C NMR spectra verified the structure of 2-1 as a hydrogen phthalate ester of the 14-hydroxyl group of oxycodone. (The absence of an $^1$H resonance in the region of 5.5–6 ppm for a $C_7$ vinylic proton, and the presence of a $^{13}$C resonance at 207.5 ppm for the $C_6$ carbonyl group excluded the presence of an enol ester linkage in 2-1.)

EXAMPLE 3

Preparation of 2-(benzyloxycarbonylamino)-pentanedioic acid 1-(3-methoxy-14-hydroxy-6,7-didehydro-4,5α-epoxy-17-methylmorphinan-6-yl) ester (3-2, also designated compound 1)

Step A: Preparation of 2-(benzyloxycarbonylamino)-pentanedioic acid 5-tert-butyl ester 1-(3-methoxy-14-hydroxy-6,7-didehydro-4,5α-epoxy-17-methylmorphinan-6-yl) ester (3-1)

A solution comprised of oxycodone free base, 1-1, (517 mg, 1.64 mmol), DIEA (1.5 mL, 8.6 mmol) in 9 mL of anhydrous acetonitrile was stirred at rt for 20 min and mixed with a solution containing DMAP (400 mg, 3.3 mmol), DCC (1.01 g, 4.1 mmol), and HOBt (440 mg, 3.3 mmol) in 6 mL of anhydrous acetonitrile. Cbz-L-Glu(OtBu)-OH (1.1 g, 3.3 mmol) was then added to the combined solutions. The mixture was stirred for 45 h at rt, precipitated DCU removed by filtration, and the solution concentrated under reduced pressure to give a dark-brown oil. HPLC analysis indicated that 39% of the oxycodone had been converted to 3-1. The brown oil containing crude 3-1 was dissolved in 20 mL of acetone, cooled in an ice bath for 2 h, and filtered to remove precipitated DCU. The filtrate was concentrated to dryness, and subjected to flash chromatography using a gradient of 0–10% methanol in DCM. The fractions containing 3-1 were combined and concentrated to dryness. The residue was treated with 20 mL acetone and filtered to remove precipitated DCU. The filtrate was concentrated to dryness under reduced pressure to yield partially purified 3-1.

Step B: Preparation of 2-(benzyloxycarbonylamino)-pentanedioic acid 1-(3-methoxy-14-hydroxy-6,7-didehydro-4,5α-epoxy-17-methylmorphinan-6-yl) ester (3-2)

The partially purified 3-1 from Step B was treated with 4 mL TFA in 2 mL DCM at rt for 10 min, dried immediately, and twice taken up in 10 mL acetonitrile and evaporated to dryness. The resulting residue was subjected to C-18 silica gel chromatography using a 20–40% gradient of acetonitrile in 0.07% aqueous TFA as eluent. Fractions containing pure 3-1 were combined to yield 105 mg (11% yield) of >99% pure (HPLC) 3-2.

EXAMPLE 4

Preparation of Fumaric Acid Mono-(3-methoxy-14-hydroxy-6,7-didehydro-4,5α-epoxy-17-methylmorphinan-6-yl) ester (4-3)

Step A: Preparation of Fumaric Acid Ethyl Ester Tert-Butyl Ester (4-1)

To a solution of fumaric acid mono-ethyl ester (721 mg, 5 mmol) and tert-butanol (0.938 mL, 10 mmol) in 10 mL of DCM was added DMAP (122 mg, 1 mmol) followed by DCC (2.06 g, 10 mmol). The resulting mixture was stirred at rt for 16 h, taken to dryness under reduced pressure, stirred overnight with 50 mL acetone and filtered to remove DCU. The resulting filtrate was concentrated under reduced pressure, and the residue taken up in EtOAc. The EtOAc was washed twice with 30 mL 0.1 M $KHSO_4$, and once with 30 mL saturated $NaHCO_3$ and once with 30 mL of brine. The resulting EtOAc solution was treated with charcoal and dried over magnesium sulfate, concentrated under reduced pressure, and subjected to silica gel flash chromatography using a gradient of 0–15% EtOAc in hexanes as eluent to give essentially pure (one peak on HPLC) 4-1 (350 mg, 35% yield).

Step B: Preparation of Fumaric Acid Mono-Tert-Butyl Ester (4-2)

4-1 (340 mg, 1.7 mmol) was stirred for 1 h at rt with a solution comprised of 4 mL THF, and 4 mL of a solution containing 1 M NaOH and 1 M LiCl. The resulting mixture was acidified to pH 3-4 with 1 M $KHSO_4$ and extracted twice with 30 mL of EtOAc. The extract was washed with 30 mL of brine, dried over magnesium sulfate, and concentrated under reduced pressure. The resulting material was subjected to silica gel flash chromatography using a gradient of 5–10% methanol in DCM to yield 240 mg (82% yield) of 4-2.

Step C: Preparation of fumaric acid mono-(3-methoxy-14-hydroxy-6,7-didehydro-4,5α-epoxy-17-methylmorphinan-6-yl) ester (4-3)

Oxycodone free base, 1-1, (13 mg, 0.04 mmol) in 0.5 mL acetonitrile was stirred with TEA (0.034 mL 0.24 mmol) for 30 min at rt. DMAP (15 mg, 0.12 mmol) and DCC (25 mg, 0.12 mmol) were then added to the solution followed by a solution comprised of 4-2 (41 mg, 0.24 mmol) in 1 mL of acetonitrile. The resulting mixture was stirred for 16 h and concentrated under reduced pressure. The resulting residue was stirred with 4 mL of acetone for 30 min, the precipitated DCU removed by filtration, and the acetone removed under reduced pressure. The residue was treated with 0.8 mL of TFA (5 min at rt) to remove the tert-butyl group. The TFA was then removed under reduced pressure and the resulting residue purified by HPLC on a C-18 column eluted with 20% acetonitrile in 0.07% aqueous TFA to yield fraction containing essentially pure 4-3.

EXAMPLE 5

Preparation of poly(ethylene glycol), Mr 2,000, methyl ether, carbonylimidodiacetic acid mono-(3-methoxy-14-hydroxy-6,7-didehydro-4,5α-epoxy-17-methylmorphinan-6-yl) ester (5-4, also designated compound 5)

Step A: Poly(Ethylene Glycol), Mr 2,000, Methyl Ether, Nitrophenyl Carbonate (5-1)

10 g (5 mmol) of poly(ethylene glycol), Mr 2,000, methyl ether was boiled with 200 mL of toluene and 100 mL of solvent distilled off to remove water. The solution was cooled to rt, 10 mL (61 mmol) of DIEA and 10 g (50 mmol) of nitrophenyl chloroformate added, and the mixture stirred overnight at 55° C. The reaction mixture was then concentrated under reduced pressure. The residue was taken up in DCM, and purified by precipitation from DCM with ethyl ether to yield 10 g of 5-1 (92%).

Step B: Preparation of Poly(Ethylene Glycol), Mr 2,000, Methyl Ether, Carbonylimidodiacetic Acid (5-2)

5-1 was added to a stirred mixture of 0.666 g (5 mmol) iminodiacetic acid, 1.9 mL (11.5 mmol) DIEA, and 20 mL of DCM. After 12 h, reverse phase HPLC of an acidified aliquot of the reaction mixture indicated essentially complete release of p-nitrophenol and consumption of 5-1. The reaction mixture was filtered, and the filtrate concentrated under reduced pressure. Ethyl ether (200 mL) was added to the concentrate to precipitate the product. 1 N HCl (50 mL) was added to dissolve the solid. After extraction the aqueous phase with DCM, the DCM was concentrated under reduced pressure. Addition of ethyl ether to the DCM concentrate yielded 5-2 (0.446 g, 45%).

Step C: Preparation of Poly(Ethylene Glycol), Mr 2,000, Methyl Ether, Carbonyliminodiacetic Anhydride (5-3)

DCC (28 mg, 0.25 mmol) was added to 5-2 (430 mg, 0.2 mmol) in 3 mL DCM. After stirring the solution for 4 h, the DCU was removed by filtration to yield a DCM solution of 5-3 which was used in Step D without further purification Step D: Preparation of Poly(Ethylene Glycol), Mr 2,000, Methyl Ether, Carbonyliminodiacetic Acid Mono-(3-methoxy-14-hydroxy-6,7-didehydro-4,5α-epoxy-17-methylmorphinan-6-yl) ester (5-4)

K-OtBu (28 mg, 0.25 mmol) was added to a stirred suspension of 1-1 (65 mg, 0.21 mmol) in 2 mL DCM under argon at −78° C. in an acetone/dry ice bath. After 40 min, the DCM solution of 5-3 from Step C (which was at rt) was added via syringe to the stirred solution of 1-1 under argon in the acetone/dry ice bath. After one hour the reaction mixture was brought to rt and neutralized with TFA. The resulting DCM solution was washed with 0.1% aqueous TFA and concentrated under reduced pressure. Purified product, 5-4, was obtained by precipitation of the DCM concentrate with ethyl ether.

EXAMPLE 6

Preparation of Poly(Ethylene Glycol), Mr 2,000, Methyl Ether, N-carbonylglutamic Acid 1-(3-methoxy-14-hydroxy-6,7-didehydro-4,5α-epoxy-17-methylmorphinan-6-yl) Ester (6-4, Also Designated Compound 4)

Step A: Preparation of Poly(Ethylene Glycol), Mr 2000, Methyl Ether, N-carbonylglutamic Acid 5-Tert-butyl Ester (6-1)

5-1 (1 g, 0.46 mmol) was added to a stirred suspension of 1.02 g (5 mmol) 2-aminopentanedioic acid 5-tert-butyl ester in 7.5 mL of 0.333 M NaOH at rt. The solution turned yellow concomitant with dissolution of 5-1. After 45 min, reverse phase HPLC indicated essentially complete consumption of 5-1 and liberation of p-nitrophenol. The reaction mixture was acidified to pH 1 with 1 N HCl, and extracted with DCM. The DCM was washed with 0.1 N HCl and concentrated under reduced pressure. Addition of ethyl ether to the DCM concentrate resulted in precipitation of 450 mg (0.202 mmol, 44%) of the desired product (6-1).

Step B: Preparation of Poly(Ethylene Glycol), Mr 2,000, Methyl Ether, N-carbonylglutamic Acid 5-Tert-butyl Ester, 1-p-nitrophenyl Ester (6-2)

6-1 (0.45 g, 0.20 mmol) and p-nitrophenol (36 mg, 0.26 mmol) were dissolved in 1 mL of DCM. The solution was cooled in an ice water bath; after which time DCC (53 mg, 0.26 mmol) was added. After 10 minutes of stirring in the ice water bath, the solution was removed from the ice water bath and stirred overnight at rt. The resulting reaction mixture was filtered to remove DCU. The DCU precipitate was washed with 5 mL of DCM, and the DCM solutions were combined and concentrated under reduced pressure. The product (6-2) was purified from the DCM concentrate by precipitation with ethyl ether to yield 168 mg (36%) of 6-2.

Step C: Preparation of Poly(Ethylene Glycol), Mr 2,000, Methyl Ether, N-carbonylglutamic Acid 5-Tert-butyl Ester, 1-(3-methoxy-14-hydroxy-6,7-didehydro-4,5α-epoxy-17-methylmorphinan-6-yl) Ester (6-3)

K-OtBu (10 mg, 0.0.086 mmol) was added to a stirred suspension of 1-1 (23 mg, 0.073 mmol) in 1 mL DCM under argon at −78° C. in an acetone/dry ice bath. After 40 min, 168 mg (0.071 mmol) of 6-2 in 1 mL DCM (which was at rt) was added via syringe to the stirred solution of 1-1 under argon in the acetone/dry ice bath. After one hour, the reaction mixture was neutralized with TFA. The resulting DCM solution was washed with 0.1% aqueous TFA and concentrated under reduced pressure. The product, 6-3, was purified by precipitation of DCM concentrates of 5-4 with ethyl ether.

Step D: Preparation of poly(Ethylene Glycol), Mr 2,000, Methyl Ether, N-carbonylglutamic Acid 1-(3-methoxy-14-hydroxy-6,7-didehydro-4,5α-epoxy-17-methylmorphinan-6-yl) ester (6-4)

5-4 was dissolved in neat TFA at rt, after 15 min the TFA was removed under reduced pressure to yield 6-4, which was purified by dissolution in DCM and precipitation with ethyl ether.

EXAMPLE 7

Preparation of Poly(Ethylene Glycol), Mr 2,000, Methyl Ether, N-carbonylglycine 1-(3-methoxy-14-hydroxy-6,7-didehydro-4,5α-epoxy-17-methylmorphinan-6-yl) ester (7-3).

Step A: Preparation of Poly(Ethylene Glycol), Mr 2,000, Methyl Ether, N-Carbonylglycine (7-1)

5-1 (1 g, 0.46 mmol) was added to a solution of glycine (0.375 g, 5 mmol) in 5 mL of 0.5 N NaOH. The solution turned yellow concomitant with dissolution of 1. After 45 min reverse phase HPLC of an acidified aliquot of the reaction mixture indicated essentially complete consumption of 5-1 and release of p-nitrophenol. The reaction mixture was acidified to pH 1 with 1 N HCl and extracted three times with 5 mL DCM. The combined DCM extract was washed with water and concentrated under reduced pressure. Addition of ethyl ether resulted in precipitation of 436 mg (0.207 mmol, 45%) of 7-1.

Step B: Preparation of Poly(Ethylene Glycol), Mr 2,000, Methyl Ether, N-carbonylglycine 1-p-nitrophenyl Ester (7-2)

7-1 (436 mg, 0.21 mmol) and p-nitrophenol (37 mg 0.27 mmol) were dissolved in 1 mL of DCM. The solution was cooled in an ice water bath and DCC (55 mg, 0.27 mmol) was added. After 10 minutes of stirring in the ice water bath, the solution was stirred overnight at rt. The solution was filtered to remove the DCU and the DCU precipitate washed with 5 mL of DCM. The DCM solutions combined, concentrated under reduced pressure and the product precipitated with ethyl ether to yield 130 mg (28%) of 7-2.

Step C: Preparation of Poly(Ethylene Glycol), Mr 2,000, Methyl Ether, N-carbonylglycine 1-(3-methoxy-14-hydroxy-6,7-didehydro-4,5α-epoxy-17-methylmorphinan-6-yl) Ester (7-3)

K-OtBu (28 mg, 0.25 mmol) was added to a stirred suspension of 1-1 (65 mg, 0.21 mmol) in 2 mL DCM under argon at −78° C. in an acetone dry ice bath. After 40 min, 130 mg 7-2 in 0.5 mL DCM (which was at rt) was added via syringe to the stirred solution of 1-1 under argon in the acetone/dry ice bath. After one hour, the reaction mixture was neutralized with TFA. The resulting DCM solution was washed with 0.1% aqueous TFA and concentrated under reduced pressure. The product, 7-3, was purified by precipitation of DCM concentrates of 7-3 with ethyl ether.

EXAMPLE 8

Preparation of Poly(Ethylene Glycol), Mr 2,000, Methyl Ether, Carboxy ((3-methoxy-14-hydroxy-6,7-didehydro-4,5α-epoxy-17-methylmorphinan-6-yl) ester) methyl ether (8-3, Also Designated Compound 8)

Step A: Preparation of Poly(Ethylene Glycol), Mr 2,000, Methyl Ether, Carboxymethyl Ether (8-1).

50 g of poly(ethylene glycol), Mr 2,000, methyl ether (25 mmol) in 750 mL of toluene was boiled and 200 mL solvent distilled off to remove water. The solution was cooled to rt and 4.5 g of KOtBu in 50 mL of t-butanol was added. The resulting mixture was stirred for 1 h at rt and 16 mL of ethyl bromoacetate added. The resulting solution was heated to reflux for 0.75 h, stirred at rt for 18 h, stirred with Celite and filtered. The reaction solvent was removed under reduced pressure, the residue taken up in 200 mL DCM and precipitated with 3.3 L of ethyl ether to yield 40 g of the ethyl ester derivative of 8-1. This material was stirred with 400 mL of 1 N sodium hydroxide for 4 h at rt, cooled in an ice water bath, acidified to pH 1 with 2 N HCl, and extracted twice with 200 mL of DCM. The DCM extract was concentrated under reduced pressure to approximately 50 mL, and added to 400 mL of ethyl ether. The resulting precipate was washed with ethyl ether and dried under reduced pressure to yield 37 g (72%) of 8-1.

Step B: Preparation of Poly(Ethylene Glycol), Mr 2,000, Methyl Ether, Carboxy (p-Nitophenyl Ester) Methyl Ether (8-2)

p-Nitrophenol (0.42 g, 3 mmol) was dissolved in a solution of 8-1 (5 g, 2.5 mmol) in 20 mL of DCM, and cooled in an ice bath. DCC (0.62 g, 3) was then added with stirring. After 10 min the solution was removed from the ice water bath and stirrred overnight at room temperature. The reaction mixture was filtered to remove DCU and the filtrate added to 400 mL of ethyl ether. The resulting precipate was collected, washed with ethyl ether and dried under reduced pressure to yield 3.4 g (~62%) of 8-1.

Step C: Preparation of Poly(Ethylene Glycol), Mr 2,000, Methyl Ether, Carboxy ((3-methoxy-14-hydroxy-6,7-didehydro-4,5α-epoxy-17-methylmorphinan-6-yl) Ester) Methyl Ether 8-3.

K-OtBu (59 mg, 0.52 mmol) was added to a stirred suspension of 1-1 (141 mg, 0.45 mmol) in 6 mL DCM under argon at −78° C. in an acetone/dry ice bath. After 40 min, 1 g (0.5 mmol) of 8-1 in 5 mL DCM (which was at rt) was added via syringe to the stirred solution of 1-1 under argon in the acetone/dry ice bath. The dry ice bath was removed and the stirred reaction mixture was allowed to come to rt over a period of 1 h. The reaction mixture was then neutralized with neat TFA, washed with 0.1% aqueous TFA, and concentrated under reduced pressure. The product, 8-3, was purified by precipitation of DCM concentrates of 8-3 with ethyl ether.

EXAMPLE 9

Binding Affinity of Prodrug of an Analgesic Drug v. the Analgesic Drug

Receptor Interactions:

Interactions of a prodrug of oxycodone with the µ, opioid receptors were assessed wherein receptor affinity was determined from inhibition of radio labeled ligand binding to membranes from C6 rat glioma cells expressing recombinant µ (rat) opioid receptor. Opioid-agonist activity was evaluated from the ability of the test article to stimulate [$^{35}$S]-GTP's binding. The data in the Table reveal that compound 1, a prodrug of oxycodone, has a substantially lower affinity for the µ receptor than does oxycodone. It is important to note that the affinity of compound 1 for the µ receptor may well be lower than that indicated by the measured $K_i$, since partial conversion of prodrug to oxycodone during the assay may have occurred.

Interactions of compound 1 and Oxycodone with opioid receptors.

| Receptor | Opioid | Affinity $K_i$ (µM) | Agonist Activity $EC_{50}$ (µM) |
|---|---|---|---|
| µ | Compound 1 | 1.21 ± 0.18 | 3.38 ± 0.29 |
| µ | Oxycodone | 0.21 ± 0.01 | 0.85 ± 0.15 |

Conclusions:
This shows that the prodrug of oxycodone, compound 1 has a lower binding affinity for the µ opioid receptor than the analgesic drug oxycodone.

EXAMPLE 10

Effect of Pancreatic Enzymes and Pepsin on the Rate of Conversion of Prodrug to Drug The half-lives for hydrolysis of prodrug to drug listed in the following table indicate that pancreatic enzymes do not markedly effect the liberation of oxycodone from compounds 4 and 5, whereas the release of oxycodone from compound 8 is markedly enhanced by pancreatic enzymes.

Effect of Pancreatin (0.5 mg/mL at 37° C., pH 7.4) and Pepsin (2 mg/mL at 37° C., pH 2) on the Half-Life for Release of Oxycodone from Prodrugs 4, 5 and 8

| Compound | Half-Life for Hydrolysis (h) | | |
|---|---|---|---|
| | no pancreatin | plus pancreatin | plus pepsin |
| 4 | 5.5 | 4.8 | 105 |
| 5 | 11 | 8 | 103 |
| 8 | 6.9 | 1 | |

CONCLUSIONS

These data indicate that it is possible to identify prodrugs which either resist or are susceptible to the action of pancreatic enzymes. By using one or two or more prodrugs with different half-lives in the digestive tract, it should be possible for one skilled in the art to obtain a desired oscillation in oxycodone concentration in the blood over the dosing interval.

What is claimed is:
1. An oxycodone prodrug having the structure
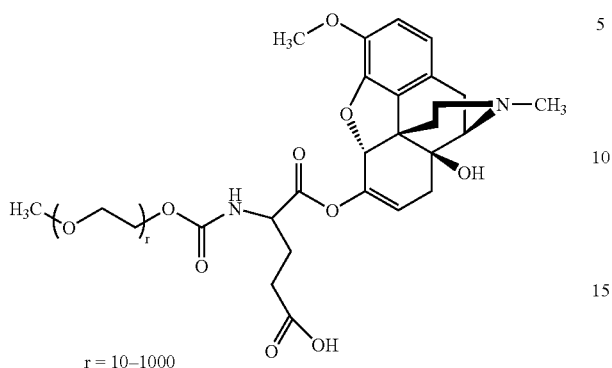
r = 10–1000
or a pharmaceutically acceptable salt thereof.
2. An oxycodone prodrug having the structure
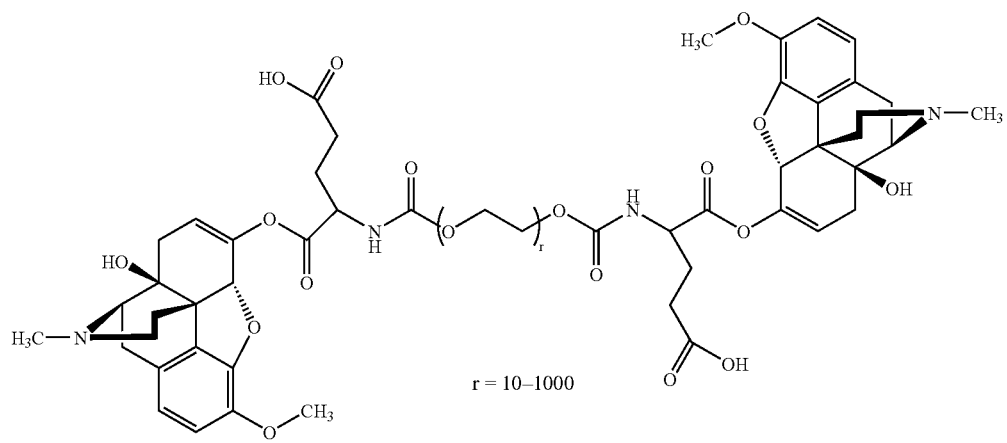
r = 10–1000
or a pharmaceutically acceptable salt thereof.
3. An oxycodone prodrug having the structure
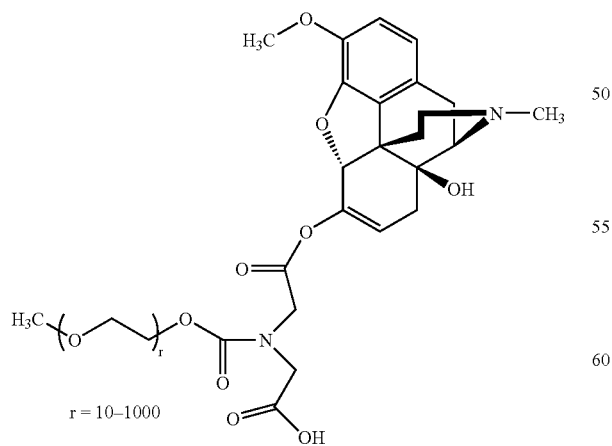
r = 10–1000
or a pharmaceutically acceptable salt thereof.

4. An oxycodone prodrug having the structure

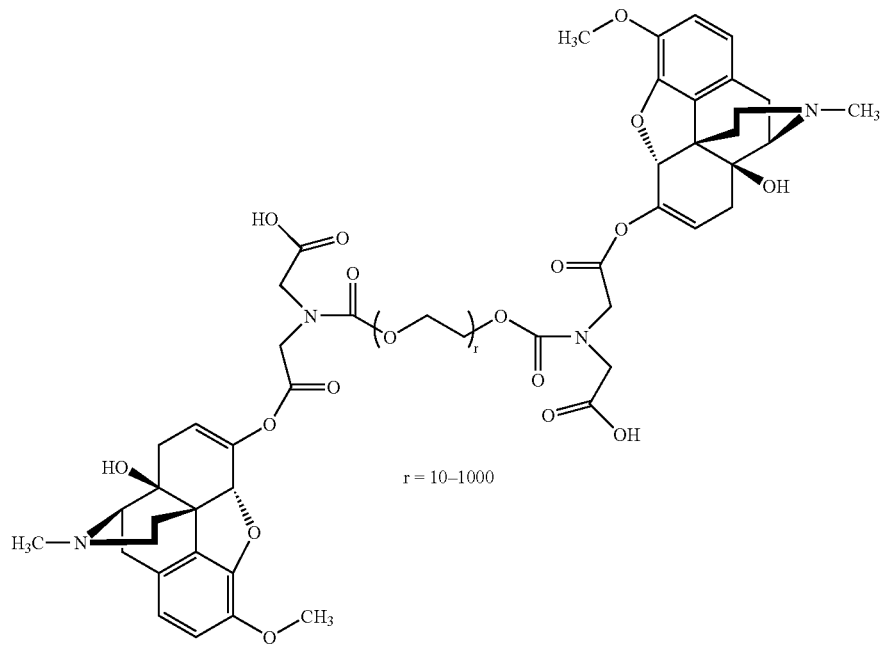

or a pharmaceutically acceptable salt thereof.

5. An oxycodone prodrug having the structure

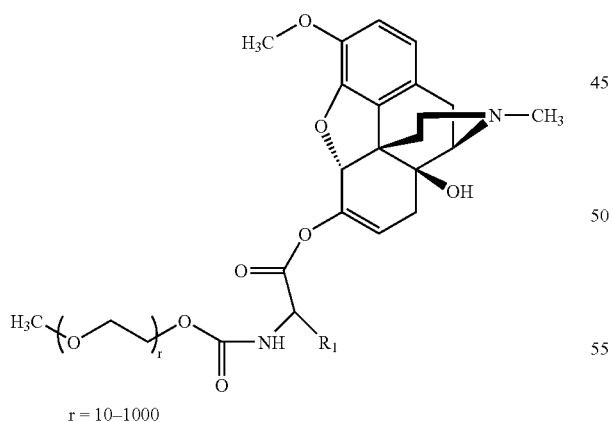

wherein, $R_1$, selected from the group consisting of:
a. hydrogen;
b. $C_{1-4}$ alkyl unsubstituted or substituted with $CH_3$ or $C_{3-7}$ cycloalkyl, or amino or guanidino or amidino or carboxy or acetamido or carbamyl or sulfonate, or phosphate or phosphonate;
c. $C_{1-4}$ alkoxy;
d. methylenedioxy;
e. hydroxy;
f. carboxy;
g. sulfonate;
h. $C_{3-7}$ cycloalkyl;
i. aryl, unsubstituted or substituted with guanidino, amidino, carboxy, acetamido, carbamyl, sulfonate, phosphate, or phosphonate; and
j. benzyl, unsubstituted or substituted with guanidino, amidino, carboxy, acetamido, carbamyl, sulfonate, phosphate, or phosphonate, or a pharmaceutically acceptable salt thereof.

6. An oxycodone prodrug having the structure

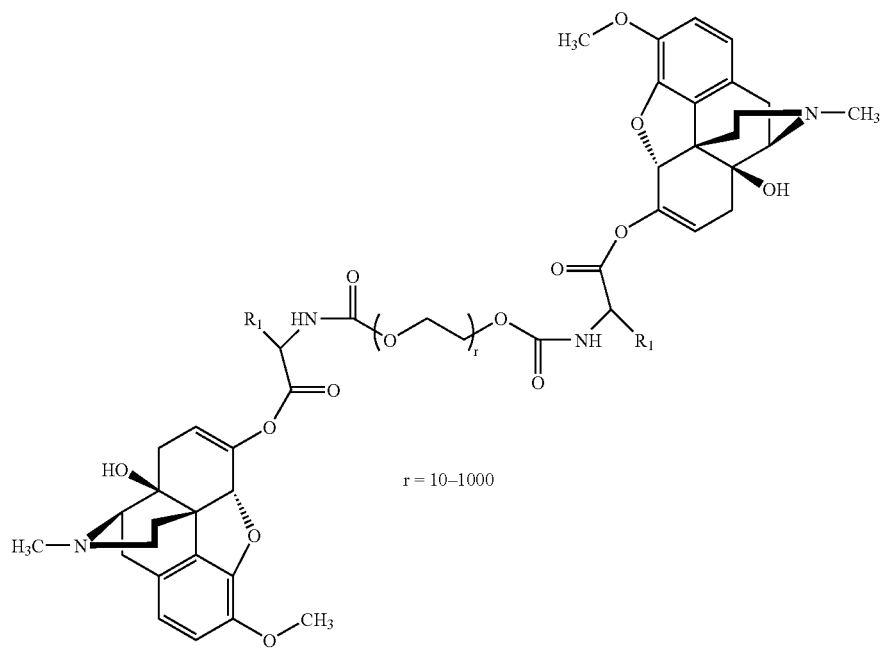

wherein $R_1$ is defined as in claim 5, or a pharmaceutically acceptable salt thereof.

7. An oxycodone prodrug having the structure

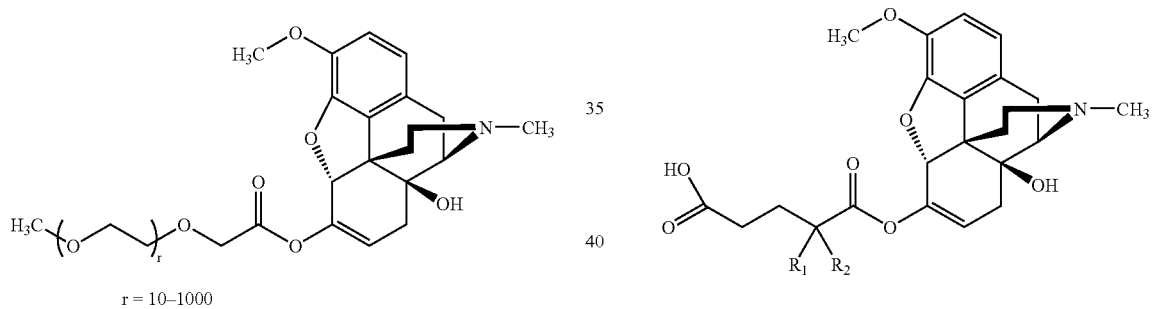

or a pharmaceutically acceptable salt thereof.

8. An oxycodone prodrug having the structure

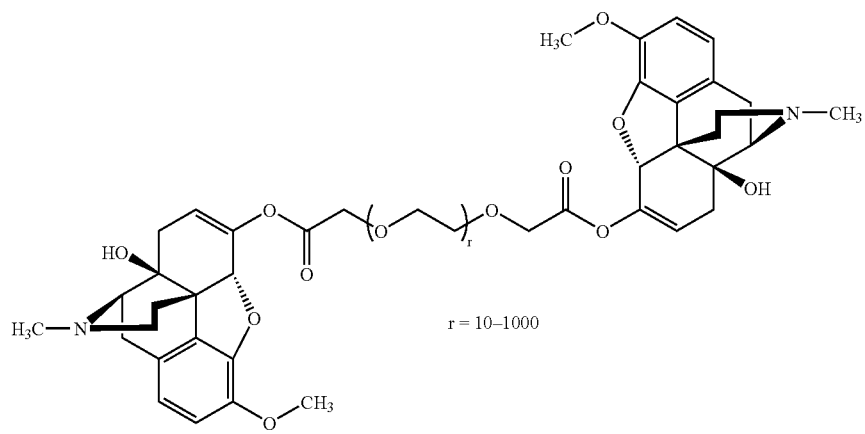

or a pharmaceutically acceptable salt thereof.

9. An oxycodone prodrug having the following structure wherein $R_1$ and $R_2$ are defined as is $R_1$ in claim 5, or a pharmaceutically acceptable salt thereof.

10. An oxycodone prodrug having the following structure

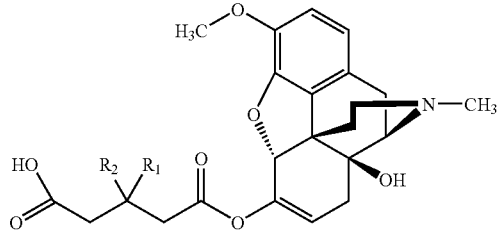

wherein R$_1$ and R$_2$ are defined as is R$_1$ in claim 5, or a pharmaceutically acceptable salt thereof.

11. An oxycodone prodrug having the following structure

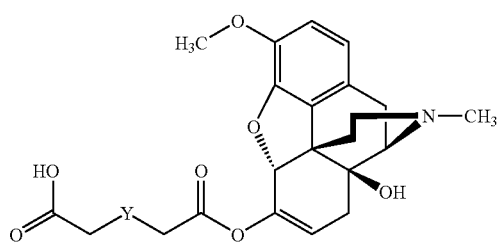

wherein Y is independently selected from the group consisting of:

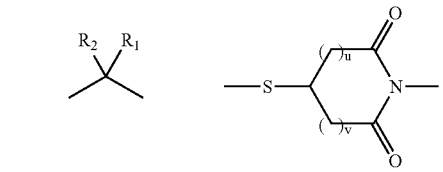

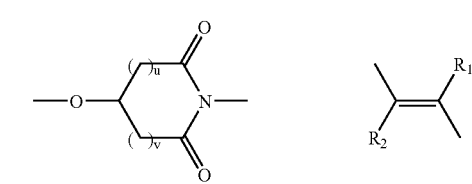

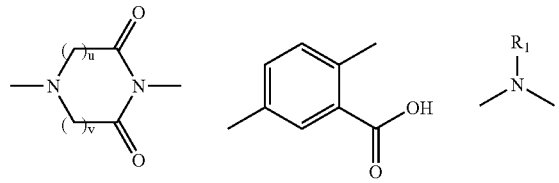

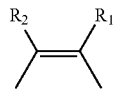

wherein the values of u and v are independently selected from the values 0, 1, 2 or 3, and wherein R$_1$ and R$_2$ are defined as is R$_1$ in claim 5, and wherein R$_4$ is independently selected from a C$_{1-4}$ alkyl group unsubstituted or substituted with CH$_3$ or C$_{3-7}$ cycloalkyl or an aryl unsubstituted or substituted with guanidino, amidino, carboxy, acetamido, carbamyl, sulfonate, phosphate, or phosphonate, or a pharmaceutically acceptable salt thereof.

12. An oxycodone prodrug having the following structure

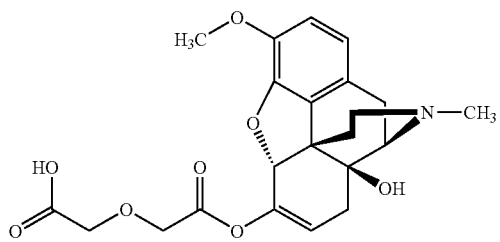

or a pharmaceutically acceptable salt thereof.

13. An oxycodone prodrug having the following structure

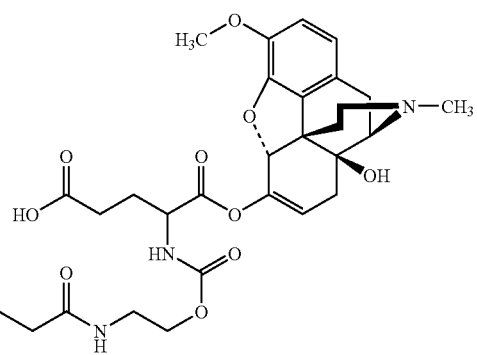

or a pharmaceutically acceptable salt thereof.

14. An oxycodone prodrug having the following structure

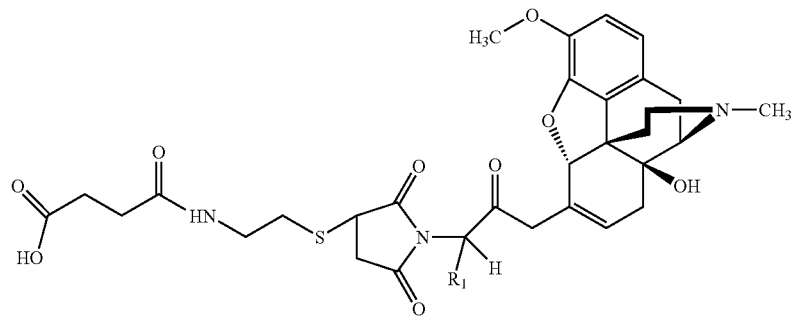

wherein $R_1$ is defined as in claim 5, or a pharmaceutically acceptable salt thereof.

15. An oxycodone prodrug having the following structure

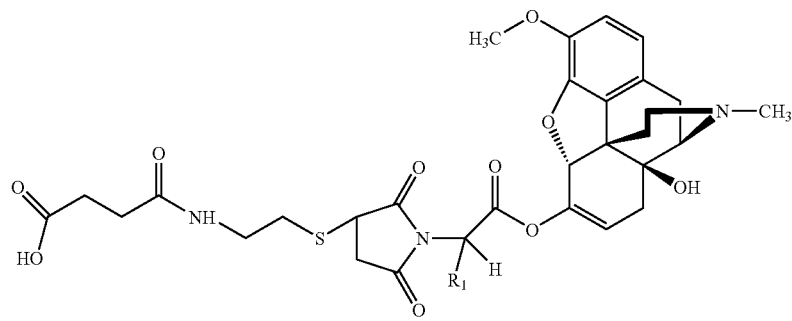

wherein $R^1$ is defined as in claim 5, or a pharmaceutically acceptable salt thereof.

16. An oxycodone prodrug having the following structure

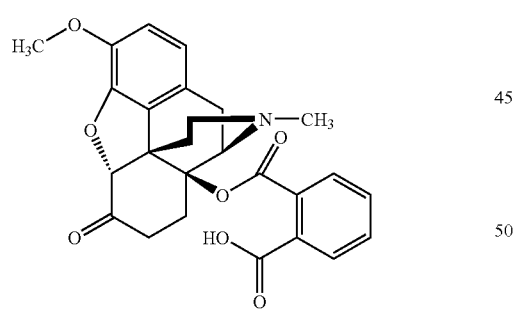

or a pharmaceutically acceptable salt thereof.

17. A pharmaceutical formulation comprising any one of the oxycodone prodrugs of claims 1–16.

* * * * *